| United States Patent [19] | [11] Patent Number: 4,731,497 |
| Grey | [45] Date of Patent: Mar. 15, 1988 |

[54] ALKYLATION OF AROMATICS WITH ALPHA-OLEFINS

[75] Inventor: Roger A. Grey, West Chester, Pa.

[73] Assignee: Atlantic Richfield Company, Los Angeles, Calif.

[21] Appl. No.: 947,120

[22] Filed: Dec. 29, 1986

[51] Int. Cl.$^4$ .................. C07C 2/64; C07C 15/107
[52] U.S. Cl. ...................... 585/455; 585/467
[58] Field of Search ...................... 585/455, 467

[56] References Cited

U.S. PATENT DOCUMENTS 4,283,573  8/1981  Young .................... 568/794
4,301,317  11/1981  Young .................... 585/455

*Primary Examiner*—Curtis R. Davis
*Attorney, Agent, or Firm*—Lewis J. Young

[57] ABSTRACT

H-mordenite has been shown to be unique in its ability to yield a high percentage of para-substitution of monoalkyl benzene by alkylation with long chain alpha-olefins. The process also yields a high percentage of substitution of the alpha-olefin in the 2-carbon position. Minimal side effects, such as dialkylation and transalkylation, are also advantages of the process.

6 Claims, No Drawings

4,731,497

ALKYLATION OF AROMATICS WITH ALPHA-OLEFINS

BACKGROUND OF THE INVENTION

The present invention relates to an improved process for the preparation of para substituted dialkyl aromatics using H-mordenite catalysts.

The alkylation of aromatic compounds with olefins using a large number of different catalysts is old in the art. Traditional catalysts include Friedel Crafts compounds, such as $AlCl_3$, $HF$, $H_2SO_4$ and $BF_3$. Recently, various zeolites have been reported as catalysts for the alkylation reaction.

U.S. Pat. No. 4,283,573 teaches to produce long chain alkylphenols by reacting alkanols with phenol in the presence of zeolite catalysts with preferential production of para-alkylphenols and placement of the phenolic moiety at the number two position on the alkyl chain. All examples which used mordenite as the catalyst, required the zeolite to be dealuminized until the silica/alumina weight ratio was increased to 93 from the initial ratio of 10. In all cases the amount of para-derivative was less than 70%.

U.S. Pat. No. 4,301,317 teaches to produce phenylalkanes by the reaction of benzene with alkenes in the presence of zeolite catalysts to produce primarily the 2-phenylalkane. Again, when mordenite was used as the zeolite catalyst, it was dealuminized to a silica/alumina ratio of 93. Although reaction with substituted benzene was mentioned, no examples were given and no indication of the isomer composition of the product was made.

SUMMARY OF THE INVENTION

I have now found that monoalkyl benzenes can be alkylated with long chain ($C_{10}$–$C_{20}$) alpha olefins at 20° to 260° C. to give predominantly para dialkyl benzenes (80–90% compared to 53% with conventional catalysts) by using fully or partially protonated mordenite catalysts having a silica to alumina ratio of from 30:1 to 2:1. The dialkyl products have a high selectivity (70–94%) for attachment of the aromatic ring at position 2 of the long alkyl chain. Transalkylation is minimized and byproduct tri- and tetra-alkylation is low ($\leq 1.0\%$).

DESCRIPTION OF THE PREFERRED EMBODIMENTS

The present process provides a means for forming para dialkylated benzenes where one of the alkyl groups is a $C_{10}$ to $C_{20}$ alkyl and where the benzene group is attached to the number 2 carbon of the long chain alkyl group.

The process comprises contacting, at a temperature of from 20° to 260° C., a monoalkyl monosubstituted benzene with an alpha olefin containing from about 10 to about 20 carbon atoms and a catalyst comprising the acid form of a three-dimensional crystalline zeolite molecular sieve having a pore size of between 6.7 and 7.5Å and having a silica:alumina weight ratio of between about 30:1 and 2:1; said benzene and alpha-olefin being in mole ratio of between about 10:1 and 3:1 and said olefin to catalyst mole ratio being from about 20:1 to 2:1; whereby the monosubstituted benzene is alkylated to at least about 80% in the paraposition and the benzene ring is attached at least about 70% at position 2 of the alpha-olefin.

Contact of the ingredients may be in a fixed bed reactor or in a slurry reactor. Flow rates in the fixed bed are not critical, but may range from 0.1 ml/hr to 36,000 ml/hr.

The reactor temperature may be from about 20° C. to about 260° C., with a preferred range of from about 100° C. to about 200° C., and an especially preferred range of from about 120° C. to about 170° C.

The monoalkyl monosubstituted benzene useful for the process may be toluene, ethylbenzene, cumene, n-propylbenzene, n-butylbenzene, sec-butylbenzene, isobutylbenzene and tert-butylbenzene.

The alpha olefins may be the various $C_{10}$ to $C_{20}$ alpha-olefins, such as 1-decene, 1-undecene, 1-dodecene, 1-tridecene, 1-tetradecene, 1-pentadecene, 1-hexadecene, 1-heptadecene, 1-octadecene, 1-nonadecene and 1-eicosene.

The molecular sieve useful as catalyst must have a pore size of between about 6.7Å and 7.5Å and have a silica:alumina weight ratio of between 30:1 and 2:1. The useful sieve is the partially or fully acid form of mordenite. Mordenite is sold primarily as the ammonium ion exchanged form which when calcined at about 500° C. gives off ammonia and leaves the strong acid, catalytically active hydrogen form. The acid activity can be readily modified by various levels of sodium ion exchange. The smaller pore size zeolites, such as ZSM-5 and 11, which have pore size of about 5.4Å are not active for the alkylation of aromatics with alpha olefins under the instant conditions. Larger pore size (13Å) zeolites, such as Y-zeolite, while active in alkylation reactions, are not as selective as H-mordenites and give about the same selectivity as traditional catalysts (53% para-dialkylation).

To minimize dialkylation (formation of trialkylated benzenes), the mole ratio of monosubstituted benzene to alpha olefin should be high, i.e., 100:1 to 1:1, preferably 10:1 to 3:1.

Similarly, the ratio of olefin to catalyst should be 100:1 to 1:1, preferably 20:1 to 2:1.

In all cases, the reactants can be diluted with an inert hydrocarbon solvent.

Under the conditions of the process, the mono alkylated benzene is alkylated to at least 80% in the paraposition and the benzene ring is attached at least 70% at the position 2 of the alpha olefin.

The major use for alkylated aromatics is in the manufacture of surfactants. These surfactants are usually produced by sulfonation of the alkylated aromatic and subsequent neutralization to form the desired sodium alkylbenzenesulfonate.

The invention is further illustrated, but not limited by, in the following examples wherein percentages are weight percent unless otherwise noted.

EXAMPLE 1

A three neck, 100 ml, round bottom flask equipped with reflux condenser, addition funnel, and magnetic stir bar was purged with argon and charged with 1 g of H-mordenite powder (obtained from Union Carbide, $SiO_2Al_2O_3 = 10:1$, calcined at 500° C. for 12 hours before use) and the Arene shown in Table I (20 g, 0.189 mol). Hexadecane, 0.2 g was added as an internal standard. The reactor was immersed in a preheated oil bath and the arene brought to reflux. The alpha olefin (0.038 mol.) shown in the Table I was added dropwise over a 30 minute period and allowed to react at 140° C. for the additional time shown in Table I. The reaction mixture was analyzed by gas chromatography. The results are shown in Table I.

TABLE I

The Alkylation of Monoalkylbenzenes Catalyzed by H—Mordenite

| Arene | Time (min) | 2-C Isomer (%) | Ring Isomers (%) | | | Alpha Olefin | Conv. (%) |
|---|---|---|---|---|---|---|---|
| | | | para | ortho | meta | | |
| Ethylbenzene | 20 | 80 | 81 | 3.3 | 15.6 | 1-dodecene | 42 |
| Ethylbenzene | 200 | 72 | 80.6 | 3.5 | 15.8 | 1-dodecene | 80 |
| Ethylbenzene | 20 | 85 | 80.2 | 3.8 | 15.7 | 1-decene | 46 |
| Ethylbenzene | 20 | 90 | 81.5 | 3.2 | 15.2 | 1-tetradecene | 33 |
| Ethylbenzene | 440 | 70.5 | 80.5 | 3.9 | 15.7 | 1-tetradecene | 80 |
| Ethylbenzene[1] | 440 | — | — | — | — | 1-dodecene | 0 |
| Toluene | 20 | 90 | 80 | 10 | 10 | 1-dodecene | 50 |
| Cumene | 20 | 83 | 84 | 1.8 | 14 | 1-dodecene | 59 |
| Cumene | 320 | 74 | 83 | 2.4 | 14.4 | 1-dodecene | 95 |

[1]HZSM-5 is substituted for H—mordenite.

As can be seen from the Table I, the yield of para-dialkylbenzene was generally 80% or better, while the percent of 2-substitution of phenyl ring to the alpha olefin was at least 70%. In all cases, less that 1% dialkylate (trialkyl benzene) was obtained in these runs and transalklylation was minimal.

EXAMPLE II

A 0.5 inch "circulating flow" fixed bed reactor was charged with 10 g of H-mordenite (1/16" extrudate pellets) and ethylbenzene (0.38 mol) containing 0.8 g. of hexadecane. At a flow ratio of 4 ml/min the reactor was heated to 140° C. and 1-dodecene (0.15 mol) was added to the circulating ethylbenzene over a 23 minute period and allowed to react for an additional 1.5 hr. The gas chromatograph analysis showed 91% conversion, a para:ortho:meta ratio of 81:2:17, and selectivity to 2-(4-ethylphenyl) dodecane of 75%. Again, less than 1% dialkylate was detected.

EXAMPLE III

To show the effect of using catalysts other than the H-mordenite of the present invention a series of experiments was run contacting 1-dodecene, ethylbenzene and various catalysts as shown in Table II for 80 minutes at 140° C. Results are shown in Table II.

TABLE II

| Catalyst | 2-C Isomer (%) | Ring Isomers (%) | | | Conv (%) | Si/Al |
|---|---|---|---|---|---|---|
| | | para | ortho | meta | | |
| H—Mordenite | 80 | 85 | 2 | 13 | 54 | 10 |
| H—Mordenite | 90 | 86 | 2 | 12 | 27 | 30 |
| H—Mordenite | 83 | 83 | 3 | 14 | 40 | 2.2 |
| NH4—Mordenite | — | — | — | — | 0 | 10 |
| Na—Mordenite | — | — | — | — | 0 | 10 |
| Mg—Mordenite | — | — | — | — | 0 | 10 |
| ZSM-5[a] | — | — | — | — | 0 | |
| ZSM-11[a] | — | — | — | — | 0 | |
| 0.5% GaZSM-5[a] | — | — | — | — | 0 | |
| Y—Zeolite[b] | 36 | 50 | 22 | 28 | 99 | |
| TiCl4[c] | 47 | 53 | 22 | 25 | 50 | — |
| AlCl3[d] | 62 | 47 | 26 | 27 | 99 | — |

[a]Small pore size (5.4%).
[b]Large pore size (13Å).
[c]Time of reaction was 20 hours.
[d]Temperature was 0° C.; for a time of 20 minutes.

From Table II, it can be seen that only the H-mordenite catalyst gave the desired para-alkylated benzene and the high percentage of 2-substituted olefin chain.

I claim:
1. A process for the alkylation of monoalkyl-monosubstituted benzenes with long-chain alpha olefins comprising:
   contacting, at a temperature of from 20° to 260° C., a monalkyl monosubstituted benzene with an alpha-olefin containing from about 10 to about 20 carbon atoms in the presence of a catalyst comprising the acid form of a three-dimensional crystalline zeolite molecular sieve having pore size of between 6.7 and 7.5Å and having a silica:alumina weight ratio of between about 30:1 and 2:1; said benzene and alpha-olefin being in mole ratio of between about 10:1 and 3:1 and said olefin to catalyst mole ratio being from about 20:1 to 2:1; whereby the alkylated benzene is alkylated to at least about 80% in the paraposition and the benzene ring is attached at least about 70% at position 2 of the alpha-olefin.
2. The process claim 1 wherein said monoalkyl monosubstituted benzene is selected from the groups consisting of toluene, ethylbenzene, cumene, n-propylbenzene, n-butylbenzene, sec-butylbenzene, isobutylbenzene and tert-butylbenzene.
3. The process of claim 1 wherein said contacting is accomplished in a slurry reactor.
4. The process of claim 1 wherein said contacting is accomplished in a fixed bed reactor.
5. The process of claim 1 wherein said catalyst is H-mordenite
6. The process of claim 1 wherein said alpha olefin is 1-decene, 1-undecene, 1-dodecene, 1-tetradecene and 1-hexadecene

* * * * *